(12) United States Patent
Watson

(10) Patent No.: US 8,439,906 B2
(45) Date of Patent: *May 14, 2013

(54) REGULATING INTERNAL PRESSURE OF A CRYOTHERAPY BALLOON CATHETER

(75) Inventor: James R. Watson, Santa Rosa, CA (US)

(73) Assignee: Boston Scientific Schimed, Inc., Maple Grove, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,722

(22) Filed: May 29, 2012

(65) Prior Publication Data

US 2012/0253337 A1    Oct. 4, 2012

Related U.S. Application Data

(63) Continuation of application No. 12/129,046, filed on May 29, 2008, now Pat. No. 8,187,261.

(51) Int. Cl.
*A61B 18/02*    (2006.01)

(52) U.S. Cl.
USPC .............................................................. 606/21

(58) Field of Classification Search ............... 606/20–26
See application file for complete search history.

(56) References Cited

U.S. PATENT DOCUMENTS

| | | | |
|---|---|---|---|
| 5,452,582 A * | 9/1995 | Longsworth | 62/51.2 |
| 6,355,029 B1 | 3/2002 | Joye et al. | |
| 6,428,563 B1 * | 8/2002 | Keller | 607/105 |
| 6,575,933 B1 | 6/2003 | Wittenberger et al. | |
| 6,575,966 B2 * | 6/2003 | Lane et al. | 606/21 |
| 6,592,577 B2 * | 7/2003 | Abboud et al. | 606/22 |
| 6,595,988 B2 * | 7/2003 | Wittenberger et al. | 606/21 |
| 2005/0215989 A1 * | 9/2005 | Abboud et al. | 606/21 |
| 2006/0095066 A1 | 5/2006 | Chang et al. | |
| 2006/0129142 A1 | 6/2006 | Reynolds | |
| 2007/0032783 A1 | 2/2007 | Abboud et al. | |

FOREIGN PATENT DOCUMENTS

EP    0850660 B1    9/2003

OTHER PUBLICATIONS

International Search Report & Written Opinion for Application No. PCT/US2009/045481, dated Aug. 3, 2009, 20 pages.

* cited by examiner

*Primary Examiner* — Linda Dvorak
*Assistant Examiner* — Daniel Fowler
(74) *Attorney, Agent, or Firm* — Seager, Tufte & Wickhem, LLC

(57) ABSTRACT

A method of performing a cryotherapy procedure can include introducing a cryotherapy balloon catheter at a treatment site inside a patient's body; regulating, during a first phase of a cryotherapy procedure, flow of cryogenic fluid to and exhaust from a distal balloon portion of the cryotherapy balloon catheter to cause an initial pressure to be maintained inside the distal balloon portion that is sufficiently high to cause an outer wall of the distal balloon portion to be pressed against body tissue at the treatment site; and regulating, during a second phase of the cryotherapy procedure, flow of cryogenic fluid to and exhaust from the distal balloon portion to cause a) a temperature inside the distal balloon portion to reach a value sufficient to deliver therapeutic levels of cryotherapy to the body tissue, and b) a second-phase pressure to be maintained that is within a threshold value of the initial pressure.

19 Claims, 5 Drawing Sheets

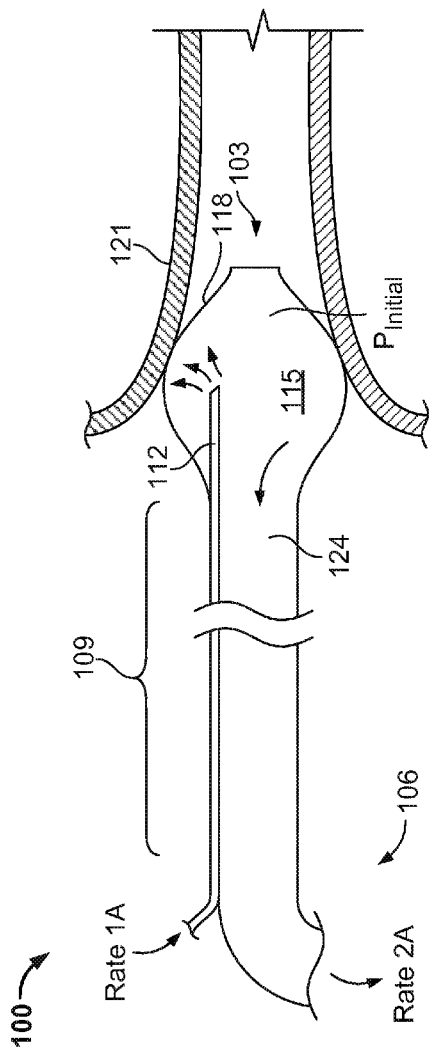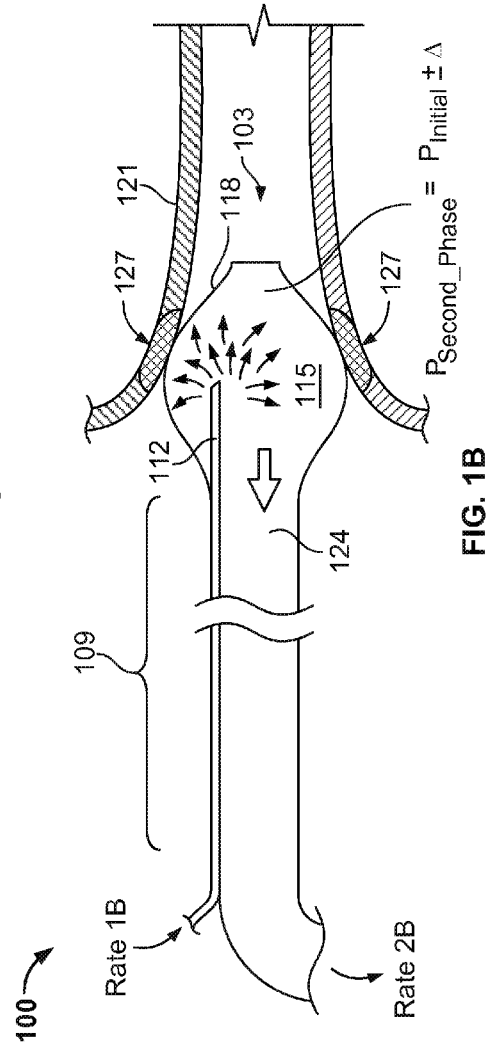

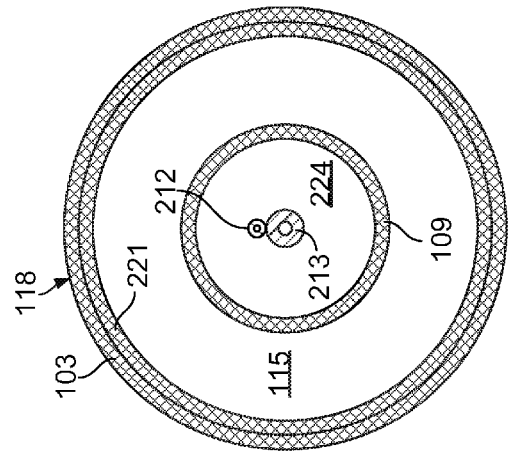
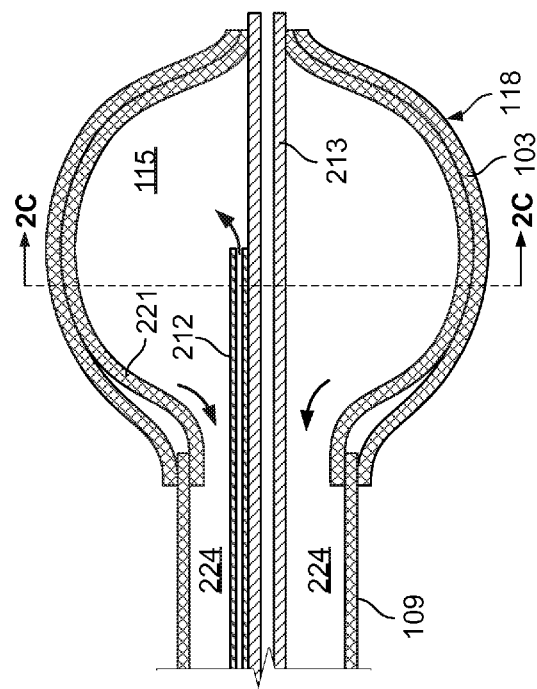
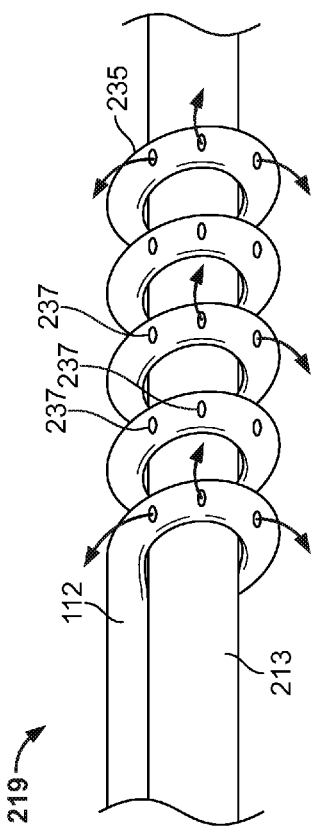
FIG. 2C
FIG. 2B
FIG. 2D

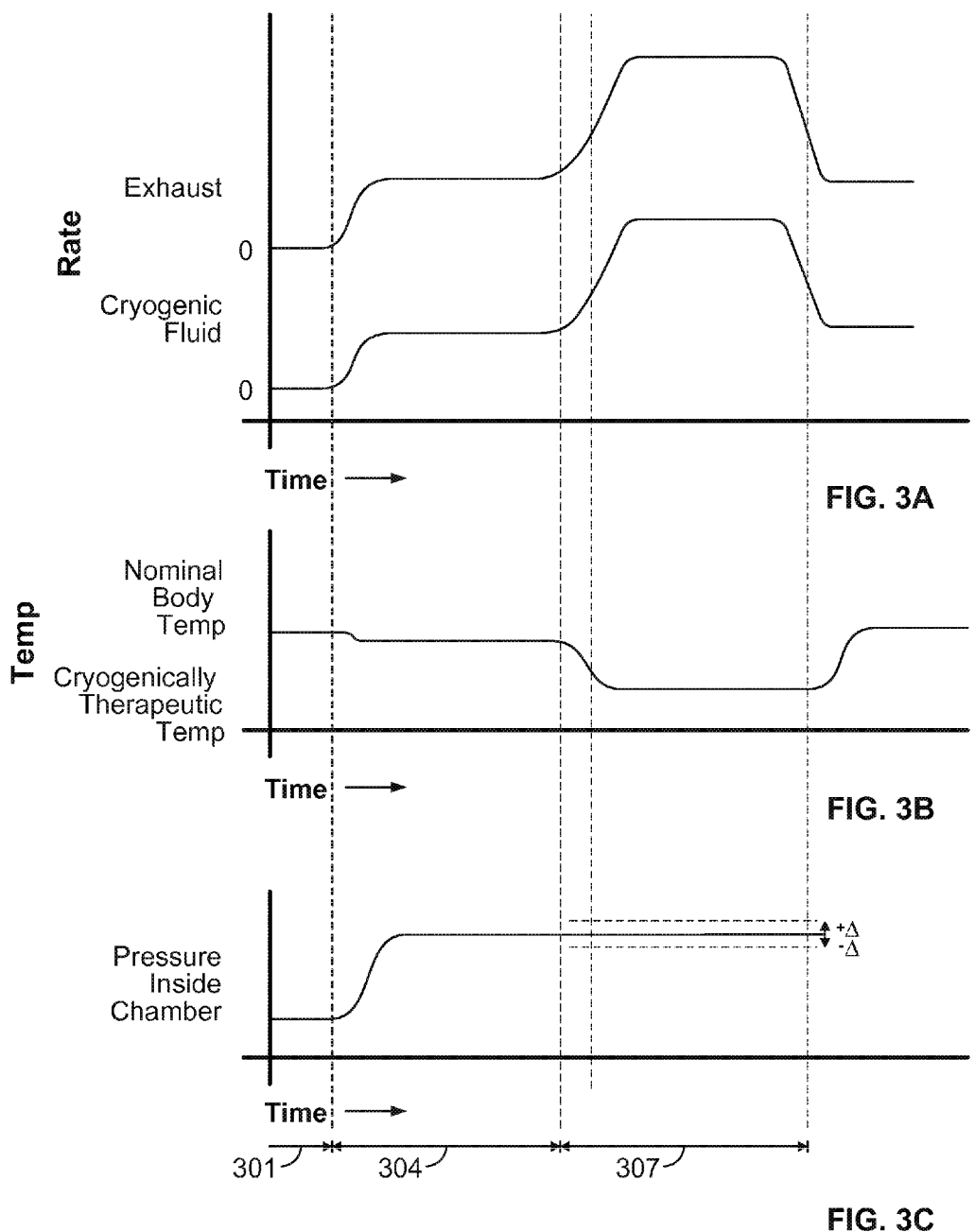

REGULATING INTERNAL PRESSURE OF A CRYOTHERAPY BALLOON CATHETER

CROSS REFERENCE TO RELATED APPLICATION

This application is a continuation of U.S. application Ser. No. 12/129,046, filed May 29, 2008, now U.S. Pat. No. 8,187,261, the disclosure of which is incorporated herein by reference.

BACKGROUND

A number of serious medical conditions may be treated in a minimally invasive manner with various kinds of catheters designed to reach treatment sites internal to a patient's body. One such medical condition is atrial fibrillation—a condition that results from abnormal electrical activity within the heart. This abnormal electrical activity may originate from various focal centers of the heart and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

One method of ablating tissue of the heart and pulmonary veins to treat atrial fibrillation is cryotherapy—the extreme cooling of body tissue. Cryotherapy may be delivered to appropriate treatment sites inside a patient's heart and circulatory system by a cryotherapy catheter. A cryotherapy catheter generally includes a treatment member at its distal end, such as an expandable balloon having a cooling chamber inside. A cryogenic fluid may be provided by a source external to the patient at the proximal end of the cryotherapy catheter and delivered distally through a lumen to the cooling chamber where it is released. Release of the cryogenic fluid into the chamber cools the chamber (e.g., through the Joule-Thomson effect), and correspondingly, the balloon's outer surface, which is in contact with tissue that is to be ablated. Gas resulting from release of the cryogenic fluid may be exhausted proximally through an exhaust lumen to a reservoir or pump external to the patient.

SUMMARY

Some cryotherapy procedures involving a cryotherapy balloon catheter include two phases. In a first phase of the cryotherapy procedure, the balloon portion of the cryotherapy balloon catheter can be initially positioned at a treatment site inside a patient. A small volume of cryogenic fluid can be delivered to inflate the balloon portion against body tissue that is to be treated during a second phase of cryotherapy. In the second phase of the cryotherapy procedure, a larger volume of cryogenic fluid can be delivered in order to lower the temperature of the balloon and the adjacent body tissue that is to be treated. In both the first and second phases, pressure inside the balloon can be controlled such that it remains at a substantially constant value. In some implementations, maintaining a substantially constant pressure inside the balloon prevents the balloon from moving away from the treatment site after it is initially positioned.

In the cryotherapy balloon catheter, cryogenic fluid can be delivered to the balloon portion through a supply lumen, and released inside the balloon portion, where it undergoes a phase change that cools the balloon portion by the Joule-Thomson effect. Gas resulting from the cryogenic fluid being released and changing phase inside the chamber can be exhausted through a separate exhaust lumen. The pressure inside the balloon portion can be controlled by regulating one or both of a rate at which cryogenic fluid is delivered and a rate at which the exhaust is extracted.

In some implementations, a method of performing a cryotherapy procedure includes introducing a cryotherapy balloon catheter at a treatment site inside a patient's body; regulating, during a first phase of a cryotherapy procedure, flow of cryogenic fluid to and exhaust from a distal balloon portion of the cryotherapy balloon catheter to cause an initial pressure to be maintained inside the distal balloon portion that is sufficiently high to cause an outer wall of the distal balloon portion to be pressed against body tissue at the treatment site; and regulating, during a second phase of the cryotherapy procedure, flow of cryogenic fluid to and exhaust from the distal balloon portion to cause a) a temperature inside the distal balloon portion to reach a value sufficient to deliver therapeutic levels of cryotherapy to the body tissue, and b) a second-phase pressure to be maintained that is within a threshold value of the initial pressure.

The threshold value may be, for example, substantially 10% of the initial pressure, substantially 5% of the initial pressure, or substantially 0.5 pounds per square inch absolute (PSIA). The initial pressure may be in the range of 10-20 pounds per square inch absolute (PSIA).

Regulating during the first phase may include regulating flow of cryogenic fluid to and exhaust from the distal balloon portion of the cryotherapy balloon catheter such that a temperature on the outer wall is maintained that does not substantially cool the body tissue beyond its nominal temperature. In some implementations, regulating during the second phase includes regulating flow of cryogenic fluid to and exhaust from the distal balloon portion of the cryotherapy balloon catheter such that the temperature on the outer wall is sustained at 80° C.+/−10° C. In some implementations, regulating during the second phase includes regulating flow of cryogenic fluid to and exhaust from the distal balloon portion of the cryotherapy balloon catheter such that a quantity of heat can be removed that is sufficient to circumferentially ablate pulmonary vein tissue of an average human adult to a depth of 5 mm within five minutes.

The method may further include regulating, after the second phase, flow of cryogenic fluid to and exhaust from the distal balloon portion such that minimal heat is extracted from the body tissue, to allow the body tissue to warm up. The method may further include at least partially deflating the distal balloon portion, introducing the cryotherapy balloon catheter to a second treatment site, and regulating the flow of cryogenic fluid to and exhaust from the distal balloon portion to repeat the first and second phases of the cryotherapy procedure at the second treatment site. Regulating flow of cryogenic fluid to and exhaust from the distal balloon portion may include regulating flow of liquid nitrous oxide to the distal balloon portion and flow of gaseous nitrous oxide from the distal balloon portion.

In some implementations, a cryotherapy catheter includes an elongate member and an inflatable balloon at a distal end of the elongate member, the elongate member having lumens formed therein to supply cryogenic fluid to a chamber of the balloon and to channel exhaust from the balloon chamber; and a controller programmed to control a first rate at which the cryogenic fluid is supplied to the balloon chamber and a second rate at which exhaust is channeled from the balloon chamber. The controller can be programmed to a) develop, during a first phase of a cryotherapy procedure, a first pressure inside the balloon chamber, at a temperature that is substantially equal to a nominal temperature of an outer wall of the inflatable balloon, and b) maintain, during a second phase of the cryotherapy procedure, a pressure inside the balloon chamber that is within a threshold value of the first pressure, at a temperature that is sufficiently low to extract heat, at a therapeutic rate, from an environment adjacent to the outer wall.

In some implementations, a diameter of the elongate member may be sized such that inflatable balloon can be routed, in a deflated state, to the left atrium of an adult human patient. The inflatable balloon may be configured to deliver, when inflated, cryotherapy to an ostium or antrum of a human patient's pulmonary vein. In some implementations, the inflatable balloon is configured to deliver cryotherapy to a human patient's prostate.

The cryotherapy catheter may further include a guidewire and corresponding guidewire lumen. A diameter of the guidewire lumen may be minimized, and a cross-sectional area of an exhaust lumen configured to channel exhaust from the balloon chamber may be maximized to maximize a possible vacuum force at a chamber end of the exhaust lumen.

The inflatable balloon may comprise a compliant material configured to enable the balloon to inflate under a pressure of 0.5 pounds per square inch (PSI) or less above an ambient pressure that is adjacent to and outside the inflatable balloon. The inflatable balloon may comprise an outer balloon and inner balloon that is separate from the outer balloon, wherein the inner balloon defines the chamber.

The details of one or more implementations are set forth in the accompanying drawings and the description below. Other features, objects, and advantages will be apparent from the description and drawings, and from the claims.

BRIEF DESCRIPTION OF DRAWINGS

FIGS. 1A and 1B illustrate details of an example cryotherapy balloon catheter that can be used to deliver cryotherapy to body tissue in first and second treatment phases, respectively.

FIGS. 2A-2D illustrate additional example details of the cryotherapy balloon catheter that is shown in FIGS. 1A and 1B.

FIGS. 3A, 3B and 3C illustrate example rate v. time, temperature v. time and pressure v. time diagrams corresponding to operation of the catheter shown in FIGS. 1 and 2A-2D.

Like reference symbols in the various drawings indicate like elements.

DETAILED DESCRIPTION

Figure 2A:
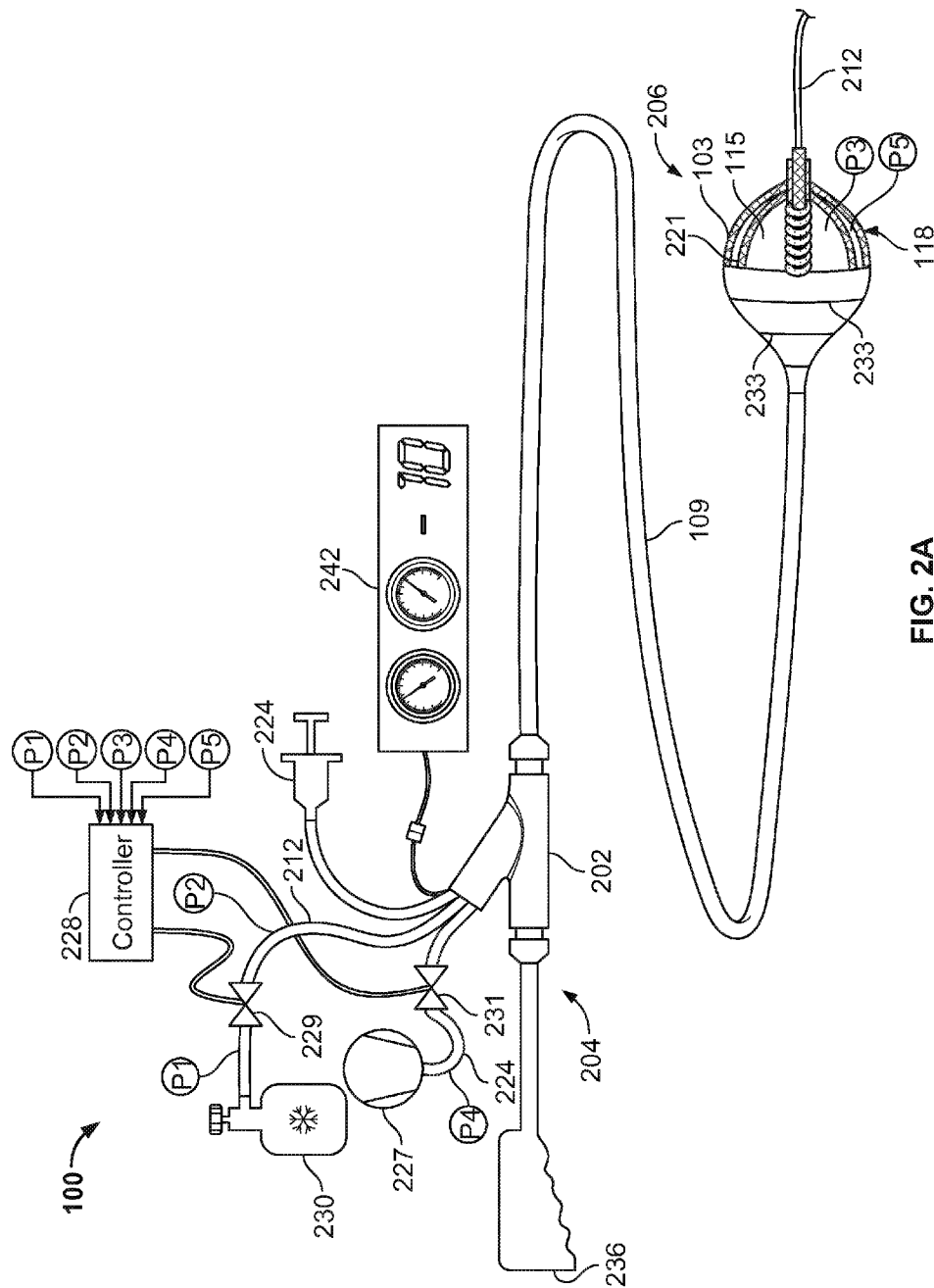

Some cryotherapy procedures involving a cryotherapy balloon catheter include two phases. In a first phase of the cryotherapy procedure, the balloon portion of the cryotherapy balloon catheter can be initially positioned at a treatment site inside a patient. A small volume of cryogenic fluid can be delivered to inflate the balloon portion against body tissue that is to be treated during a second phase of cryotherapy. In the second phase of the cryotherapy procedure, a larger volume of cryogenic fluid can be delivered in order to lower the temperature of the balloon and the adjacent body tissue that is to be treated. In both the first and second phases, pressure inside the balloon can be controlled such that it remains at a substantially constant value. In some implementations, maintaining a substantially constant pressure inside the balloon prevents the balloon from moving away from the treatment site after it is initially positioned. In this context, a substantially constant value can include, for example, values that vary by 25% or less, 10% or less, 5% or less, 0.5% or less, etc.; and "substantially" can, for example, refer to "within 25%," "within 10%," "within 5%," "within 0.5%," etc.

In the cryotherapy balloon catheter, cryogenic fluid can be delivered to the balloon portion through a supply lumen, and released inside the balloon portion, where it undergoes a phase change that cools the balloon portion by the Joule-Thomson effect. Gas resulting from the cryogenic fluid being released and changing phase inside the chamber can be exhausted through a separate exhaust lumen. The pressure inside the balloon portion can be controlled by regulating one or both of a rate at which cryogenic fluid is delivered and a rate at which the exhaust is extracted.

FIGS. 1A and 1B illustrate example details of a cryotherapy balloon catheter 100 that can be used to deliver cryotherapy. FIGS. 1A and 1B further depict an example first treatment phase (FIG. 1A) and second treatment phase (FIG. 1B) in which the cryotherapy can be delivered. Additional details of the example cryotherapy balloon catheter 100 are described below with reference to FIGS. 2A-2D.

The cryotherapy balloon catheter 100 of FIGS. 1A and 1B has a distal cryotherapy balloon 103 that can be inserted into a body lumen of a patient, such as, for example, a blood vessel or other internal body structure. More particularly, for example, the distal cryotherapy balloon 103 can be inserted (in a deflated state), through appropriate blood vessels, into a patient's heart, and specifically into the patient's left atrium (e.g., through the femoral vein, inferior vena cava, right atrium, trasseptal wall and into the left atrium). Once in the patient's left atrium, the cryotherapy balloon can be employed to ablate tissue of the pulmonary veins (e.g., tissue at the ostium or antrum of one or more pulmonary veins) in order to eliminate aberrant electrical signals that may be causing atrial fibrillation in the patient. Similarly, the cryotherapy balloon catheter 100 can be routed to other treatment sites inside a patient and employed to treat other conditions, such as cancer of the prostate. During whatever treatment is performed, a proximal end 106 of the cryotherapy balloon catheter 100 remains outside the patient.

Between the proximal end 106 and the distal cryotherapy balloon 103 is an elongate member 109 (e.g., a catheter shaft) having various internal lumens, including a supply lumen 112 for delivering a cryogenic fluid to the distal cryotherapy balloon 103. The cryogenic fluid can be released into a chamber 115 of the balloon 103, where it undergoes a phase change to a gas. As a result of the phase change, heat is extracted from the surroundings of the chamber 115, thereby cooling the surface 118 of the balloon 103 and body tissue 121 that is in contact with the surface 118 (e.g., via the Joule-Thomson effect). The elongate member 109 includes an exhaust lumen 124 for exhausting the resulting gas from the chamber 115.

During an example first phase of a cryotherapy procedure, depicted in FIG. 1A, the balloon 103 is positioned at a treatment site and inflated against body tissue 121 (e.g., a patient's pulmonary vein). To inflate the balloon, cryogenic fluid can be delivered at a low flow rate to the balloon chamber 115 (e.g., at a rate $RATE_{1A}$), and exhaust can be channeled out of the chamber 115 at a corresponding low flow rate (e.g., at a rate $RATE_{2A}$).

The flow rates of cryogenic fluid into the chamber 115 and exhaust out of the chamber 115 can be controlled such that a pressure inside the chamber 115 ($P_{INITIAL}$) is developed that is sufficient to push the outer surface 118 of the balloon 103 against the body tissue 121 that is to be treated. Volume of the cryogenic fluid that is delivered to the chamber can be minimized, such that little heat is extracted from the body tissue 121. That is, the cryogenic fluid can be delivered in the first phase primarily to develop the initial pressure necessary to inflate the balloon, rather than to cool the balloon 103 and tissue adjacent to the balloon.

During an example second phase of a cryotherapy procedure, depicted in FIG. 1B, a relatively larger volume of cryogenic fluid can be supplied to the chamber 115 in order to cool the surface of the balloon 118 (e.g., via the Joule-Thomson effect) and thereby extract heat from the adjacent body tissue 121 at a therapeutic rate (e.g., a rate at which a desired amount of tissue is cooled to a therapeutically low temperature, such as −10° C. to −90° C.). As depicted in FIG. 1B, regions 127 of body tissue can be cooled by the larger volume of cryogenic fluid, as that cryogenic fluid changes phase to a gas.

The higher flow rate of cryogenic fluid (e.g., $RATE_{1B}$) in the second phase can be balanced by a correspondingly higher flow rate of exhaust (e.g., $RATE_{2B}$), such that the pressure inside the chamber 115 during the second phase ($P_{SECOND\_PHASE}$) is very close to the initial pressure (e.g., within a threshold value, $\Delta$, such that $P_{SECOND\_PHASE} = P_{INITIAL} +/- \Delta$). In some implementations, the threshold value, $\Delta$, is a relatively small percentage of the initial pressure, such as 1% or less, 5%, 10%, 25%, etc.

Regulating the flow of cryogenic fluid to and exhaust from the distal balloon portion 103 such that internal pressures in the first and second phases are substantially constant (e.g., within a threshold value, $\Delta$, of each other) may reduce the likelihood that the balloon portion 103 will move relative to tissue that is to be treated inside a patient. If the pressure is not controlled in this manner, the balloon 103 may, in some implementations, become dislodged from its initial position if and when pressure inside the balloon changes significantly. This can be especially true in some implementations in which the tissue to be treated is in a natural state of movement during the treatment procedure. For example, in the case of cryotherapy treatment involving a patient's pulmonary veins, cryotherapy is typically delivered when the patient's heart is beating and the ostia of the pulmonary veins are also moving with each beat. By maintaining the pressure inside the balloon portion at a relatively constant value between initial positioning and treatment phases, the balloon portion may be less likely to become dislodged from its initial location than if the pressures between the initial positioning phase and the treatment phase are not actively controlled. Moreover, the balloon portion 103 may be less likely to become dislodged during the initial stages of the treatment phase, when the balloon portion 103 may have started to freeze to the body tissue. Minimizing movement at this point can be particularly important to avoid tearing the body tissue being treated.

Additional details of the example cryotherapy catheter 100 are now described with reference to FIGS. 2A-2D. As described above, the cryotherapy catheter 100 includes an elongate member 109 that has an inflatable balloon 103 at a distal end 206. The balloon 103 has an internal chamber 115 to which cryogenic fluid is delivered to cool the internal chamber 115, the external surface 118 of the balloon 103, and adjacent body tissue. A port device 202 is attached to a proximal end 204 of the elongate member 109. The port device 202 provides connections to various external equipment, including a cryogenic fluid source 230 and an exhaust pump 227.

The catheter's internal lumens allow cryogenic fluid to be delivered distally from the external cryogenic fluid source 230 to the internal chamber 115 of the balloon 103. In addition, the internal lumens of the elongate member 109 allow exhaust resulting from delivery of cryogenic fluid to the internal chamber 115 of the balloon 103 to be delivered proximally from the internal chamber 115 to the external exhaust pump 227. During operation, there may be continuous circulation within the elongate member 109 of cryogenic fluid distally and exhaust proximally.

A controller 228 can regulate flow of cryogenic fluid to the internal chamber 115 of the balloon 103 ("the balloon 103" in portions of the description that follow) and flow of exhaust from the balloon. In particular, for example, the controller 228 can, in one implementation as shown, regulate a valve 229 that controls flow of the cryogenic fluid from the cryogenic fluid source 230. The cryogenic fluid source 230 can be, for example, a pressurized flask of cryogenic fluid, such as nitrous oxide or another suitable cryogenic fluid. In other implementations (not shown), the controller controls a pump and/or pump valve combination to deliver cryogenic fluid to the internal chamber of the balloon. Similarly, the controller 228 can regulate a valve 231 and/or vacuum pump 227 to regulate flow of exhaust from the balloon 103.

By controlling both the rate at which cryogenic fluid is delivered to the balloon 103 and the rate at which exhaust is extracted from the balloon 103, the controller 228 can develop and maintain a pressure inside the balloon 103 at a number of different temperatures. For example, when cryogenic fluid is delivered at a very low rate to the balloon 103, and exhaust is similarly extracted at a very low rate, the balloon 103 may be inflated, but very little heat (if any) may be extracted from the balloon 103 or from body tissue that is in contact with the balloon. As another example, when cryogenic fluid is delivered at a higher rate, a greater amount of heat can be extracted from the balloon 103 and from body tissue that is in contact with the balloon. Varying the rate at which exhaust is extracted from the balloon 103 relative to the rate at which the cryogenic fluid is supplied to the balloon can control the pressure. In particular, for example, for a given rate at which the cryogenic fluid is supplied to the balloon 103, extracting exhaust at a higher rate will generally result in a lower pressure inside the balloon, and extracting exhaust at a lower rate will generally result in a higher pressure inside the balloon.

To precisely control pressures or flow rates, the controller 103 can employ either or both of open- or closed-loop control systems. For example, in some implementations, a rate at which cryogenic fluid (e.g., the position of the valve 229) is delivered to the balloon can be controlled with an open-loop control system, and a rate at which exhaust is extracted from the balloon 103 (e.g., the position of the valve 231 or force exerted by the pump 227) can be controlled with a closed-loop control system. In other implementations, both rates can be controlled by closed-loop control systems.

In a closed-loop control system, some feedback mechanism is provided. For example, to control the rate at which cryogenic fluid is supplied to the balloon 103, the controller 228 can employ one or more pressure sensors, such as pressure sensors P1 and P2 on either side of the control valve 229. In such an arrangement, sensor P1 can be employed to confirm an adequate supply of cryogenic fluid, and sensor P2 can be employed for closed-loop control of the supply valve 229. The controller 228 can be programmed to control a flow rate of cryogenic fluid based on the pressure measured by sensor P2 and further based on a size and resistance to flow of a supply lumen (e.g., supply lumen 212, shown in FIG. 2B). In other implementations, the controller 228 can employ both pressure sensors P1 and P2 to obtain a differential pressure measurement, and the controller can use the differential pressure measurement to control flow of cryogenic fluid to the balloon 103.

Additional sensors can be employed to regulate flow of exhaust (e.g., exhaust gas resulting from cryogenic fluid changing state inside the balloon 103) out of the balloon 103. Indirectly, such regulated flow of exhaust out of the balloon 103, in combination with the regulated flow of cryogenic fluid into the balloon, can control the pressure inside the chamber 115. In particular, the controller 228 can employ one or more pressure sensors, such as, for example, a pressure sensor P3 inside the chamber 115 and/or a pressure sensor P4 at the proximal end of an exhaust lumen (e.g., exhaust lumen 224).

A cryotherapy catheter may employ additional sensors. For example, the cryotherapy catheter 100 is depicted as having a fifth pressure sensor, P5, between an internal balloon 221 that forms the chamber 115 and an external balloon 103 that comes into contact with body tissue that is to be treated. Such a two-layer or two-balloon approach may provide a safety benefit. In particular, for example, if either the internal balloon 221 or external balloon 103 is compromised, cryogenic fluid and gas inside the balloons can be isolated from the patient's body. In some implementations, the fifth sensor can indicate whether both internal balloon 221 and external balloon 103 are intact. In such implementations, a vacuum can be drawn between the balloons 221 and 103, such that the surfaces of the two balloons may be in contact under normal conditions. Under normal conditions, sensor P5 may typically detect a pressure corresponding to a fixed vacuum. If the inner balloon 221 bursts, the pressure sensor P5 may detect a positive pressure; if the outer balloon 103 bursts, the pressure sensor P5 may detect less of a vacuum than before the outer balloon 103 burst. Various other pressure sensors (not shown) may be employed in other implementations.

Pressure sensors P1-P5 are graphically depicted at points corresponding to where pressure may be measured. Physically, a pressure sensor (or transducer) can disposed in the catheter 100 where depicted, and electrical signals from the sensor or transducer can be routed to appropriate equipment at the proximal end 204 of the catheter 100. Alternatively, one or more pressure transducers can be disposed at the proximal end 204 of the catheter 100, and the transducers can be fluidly coupled to points at which a pressure measurement is desired (e.g., points corresponding to the depicted locations in FIG. 2A) by pressure lumens (not shown). Other pressure sensor or transducer arrangements are contemplated.

Individual pressure sensors can measure pressure in different ways. In some implementations, each sensor measures absolute pressure, for example, in pounds per square inch absolute (PSIA). In such implementations, two pressure sensors may typically be used to obtain a differential measurement that inherently eliminates any effect of local atmospheric pressure (e.g., ambient pressure). For example, if P1 and P2 are absolute pressure sensors in the catheter 100, the controller 228 can employ both P1 and P2 to differentially determine a pressure in the supply lumen 212. In other implementations, each pressure sensor may measure pressure relative to an ambient pressure (e.g., a pressure outside and generally adjacent to the patient, or put another way, the atmospheric pressure next to the patient, given the patient's altitude and relevant atmospheric conditions of the air surrounding the patient), which may itself be measured a separate sensor (not explicitly shown). Another sensor may be employed to measure ambient pressure at one or more points inside the patient's body (e.g., to compensate for blood pressure or other internal pressures).

In some implementations, as mentioned above, pressure inside the balloon 103 can be primarily controlled by controlling the rate at which exhaust is extracted from the balloon 103. Temperature inside the balloon 103, on the other hand, may depend on control of both the flow of cryogenic fluid and the flow of exhaust. That is, for a given pressure inside the balloon, a larger amount of cryogenic fluid supplied, and corresponding amount of exhaust removed may result in a lower temperature on the surface 118 of the balloon 103, than would result from a smaller amount of cryogenic fluid being supplied to the balloon 103 with a corresponding smaller amount of exhaust removed from the balloon to maintain the same pressure.

The controller 228 itself can take many different forms. In some implementations, the controller 228 is a dedicated electrical circuit employing various sensors, logic elements and actuators. In other implementations, the controller 228 is a computer-based system that includes a programmable element, such as a microcontroller or microprocessor, which can execute program instructions stored in a corresponding memory or memories. Such a computer-based system can take many forms; include various input and output devices; and may be integrated with other system functions, such as monitoring equipment 242 (described in more detail below), a computer network, other devices that are typically employed during a cryotherapy procedure, etc. For example, a single computer-based system may include a processor that executes instructions to provide the controller 228 function, display imaging information associated with a cryotherapy procedure (e.g., from an imaging device); display pressure, temperature and time information (e.g., elapsed time since a given phase of treatment was started); and serve as an overall interface for a medical practitioner who uses the cryotherapy catheter 100. In general, various types of controllers are possible and contemplated, and any suitable controller 228 can be employed.

The catheter 100 shown in FIG. 2A is an over-the-wire type catheter. Such a catheter 100 employs a guidewire 212, extending from the distal end 206 of the catheter 100. In some implementations, the guidewire 212 may be pre-positioned inside a patient's body. Once the guidewire 212 is properly positioned, the balloon 103 (in a deflated state) and the elongate member 109 can be routed over the guidewire 212 to a treatment site. In some implementations, the guidewire 212 and balloon portion 103 of the catheter 100 may be advanced together to a treatment site inside a patient's body, with the guidewire portion 212 leading the balloon 103 by some distance (e.g., several inches). When the guidewire portion 212 reaches the treatment site, the balloon 103 may then be advanced over the guidewire 212 until it also reaches the treatment site. In over the-wire implementations, as shown, the cryotherapy catheter 100 includes a guidewire lumen 213, which allows the balloon 103 to be routed to a treatment site inside a patient over a pre-positioned guidewire (see, for example, FIG. 2C). Other implementations are contemplated, such as steerable catheters that do not employ a guidewire. As depicted in one implementation, the catheter 100 includes a manipulator 236, by which a medical practitioner may navigate the guidewire 212 and balloon 103 through a patient's body to a treatment site.

In some implementations, release of cryogenic fluid into the cooling chamber can inflate the balloon 103 to a shape similar to that shown in FIG. 2A. In other implementations, a pressure source 224 can be used to inflate the balloon 103 independently of the release of cryogenic fluid into the internal chamber 115 of the balloon 103. The pressure source 224 may also be used to inflate an anchor member on the end of the guidewire 212 (not shown).

The catheter 100 includes a connector for connecting monitoring equipment 242. The monitoring equipment may be used, for example, to monitor temperature or pressure at the distal end of the catheter 100.

To aid in positioning the treatment member 103 of the catheter 100 inside a patient's body, various marker bands 233 can also be disposed at the distal end 206 of the catheter 100. The marker bands 233 may be opaque when the catheter is viewed by x-ray or other imaging techniques.

In some implementations, the balloon 103, and a corresponding separate internal cooling chamber, if present (e.g., balloon 221, shown in FIG. 2A), may be formed from a polymer including, but not limited to, polyolefin copolymer, polyester, polyethylene teraphthalate, polyethylene, polyether-block-amide, polyamide, polyimide, nylon, latex, or urethane. For example, certain implementations of the balloon 103 comprise PEBAX® 7033 material (70D poly ether amide block). The balloon 103 may be made by blow-molding a polymer extrusion into the desired shape. In some implementations, the balloon 103 may be constructed to expand to a desired shape when pressurized without elastically deforming substantially beyond the desired shape.

A number of ancillary processes may be used to affect the material properties of the balloon 103. For example, a polymer extrusion may be exposed to gamma radiation which can alter the polymer infrastructure to provide uniform expansion during blow molding and additional burst strength when in use. In addition, the molded balloon 103 may be exposed to a low temperature plasma field which can alter the surface properties to provide enhanced adhesion characteristics. Those skilled in the art will recognize that other materials and manufacturing processes may be used to provide balloon 103 (and any internal balloon(s)) suitable for use with the catheter 100.

FIG. 2B shows a longitudinal cross-section of the example cryotherapy balloon 103 and an example elongate member 109 through which cryogenic fluid and exhaust can be cycled to and from the internal chamber 115 of the cryotherapy balloon 103. As depicted in FIG. 2B, cryogenic fluid can be delivered from an external source (e.g., 230 in FIG. 2A) to a cooling chamber 115 internal to the balloon 103, via a coolant delivery lumen 112. The coolant can be released into the cooling chamber 115 from an opening at the end of the delivery lumen 112, or the coolant can be released through a cryotherapy device 219 (see FIG. 2D) disposed at the end of the delivery lumen 112. In implementations in which it is present, the cooling device 219 can include a coiled extension 235 having a number of apertures 237 from which pressurized liquid coolant can escape and change state to a gas. When released, the coolant can undergo a phase change, cooling the chamber 115 via the Joule-Thomson effect, as well as cooling the external surface 118 of the outermost balloon 103 and a patient's body tissue that is adjacent to the external surface 118 of the outer balloon. The cryogenic fluid, or gas if the fluid has undergone a phase change, can then be exhausted through an exhaust lumen 224 to a reservoir, pump or vacuum source external to the catheter (e.g., 227 in FIG. 2A). In some implementations, the exhaust lumen 224 can be defined generally by the outer layer of the elongate shaft 109, as shown. In other implementations, the catheter can include one or more dedicated exhaust lumen structures (not shown) that are defined independently of the elongate member 109.

The coolant that is cycled into the balloon 115 is typically one that will provide the appropriate heat transfer characteristics consistent with the goals of treatment. In some implementations, liquid $N_2O$ (nitrous oxide) can be used as a cryo coolant. When liquid $N_2O$ is used, it can be transported to the cooling chamber 115 in the liquid phase where it changes to a gas at the end of the coolant delivery lumen 112, or from the apertures 237 of a cooling device 219. Other implementations may use Freon, Argon gas, and $CO_2$ gas, or other agents as coolants.

In some implementations, as shown and briefly described above, a second balloon 221 is provided within the outer balloon 103 to isolate the cryogenic fluid within the cooling chamber 115. In such implementations, the outer balloon 103 forms a safety chamber that prevents coolant from escaping if the cooling chamber 115 balloon 821 bursts. A separate vacuum lumen (not shown) may be provided to evacuate any gas or liquid that escapes from the internal cooling chamber 115. In operation, the outer and inner balloons 103 and 821 may expand and deflate together. In some implementations, release of coolant inflates the balloons 103 and 821. In some implementations, the balloons 103 or 821 are first inflated by the injection of an inflation fluid or gas (e.g., a saline solution or an inert gas), after which the coolant may be introduced to the cooling chamber 115.

FIG. 2C shows a radial cross-section along the line A-A that is shown in FIG. 2B. As shown in FIG. 2C, the coolant delivery lumen 212 is adjacent to the guidewire lumen 213, and the guidewire lumen 213 is shown to be substantially coaxial with the exhaust lumen 224, which corresponds to the overall shaft (e.g., elongate member 109) of the catheter. In some implementations, the cross-sectional area of the exhaust lumen 224 is maximized, to permit the greatest possible vacuum at the chamber. To maximize the area, the guidewire lumen 213 can be minimized or omitted, and other unnecessary lumens can be omitted. By maximizing the cross-sectional area and resulting maximum possible vacuum force at the chamber 115 of the balloon 103, pressure inside the balloon may, in some implementations, be more easily controlled. Moreover, with a compliant balloon material (see additional detail below), the pressure inside the balloon during different phases of cryotherapy treatment can be minimized to only a fraction of a PSI over ambient pressure, which may further reduce the possibility that the balloon will become dislodged from its initial position.

In some implementations, lumens can have other arrangements, and more or fewer lumens can be included in the catheter. For example, the coolant delivery lumen 212 may be disposed coaxially around the guidewire lumen 213; the guidewire lumen 213 may be omitted in a steerable catheter design; lumens for steering members may be provided; one or more vacuum lumens may be included; one or more exhaust lumens may be included that are independent of the outer layer of the catheter shaft 109; additional lumens may be provided for inflating or deflating the balloons 103 or 221 or for inflating or deflating other balloons not shown in FIG. 2A, 2B or 2C; and additional lumens may be provided to control an anchor member that may be disposed on a guidewire near the distal portion of the balloon 103.

FIGS. 3A, 3B and 3C illustrate rate v. time, temperature v. time and pressure v. time diagrams corresponding to operation of the catheter 100 shown in FIGS. 1 and 2A-2D, according to one example implementation. In all three figures, a time period 301 depicts a preliminary phase, during which the balloon catheter 100 can be positioned at a treatment site inside a patient; a time period 304 depicts a first phase, during which the balloon portion 103 of the catheter 100 is inflated against tissue to be treated; and a time period 307 depicts the second phase of an example cryotherapy procedure, during which cryotherapy can be delivered to appropriate body tissue while the internal pressure of the balloon 103 can be maintained at a relatively constant level.

As depicted in FIG. 3A, rates at which cryogenic fluid is supplied to the balloon 103 during the preliminary phase (period 301) are substantially zero. That is, as the balloon portion 103 of the catheter 100 is positioned, the balloon 103 is generally deflated. In some implementations, in addition to being deflated, the balloon may be enclosed by an introducer sheath or other structure of the catheter 100. The flow of exhaust out of the balloon is also substantially zero, although a slight vacuum may be drawn in some implementations in order to ensure that the balloon 103 remains deflated during the initial positioning phase. During this time, as depicted in FIG. 3B, temperature of the balloon 103 is substantially equal to the nominal body temperature of the patient (e.g., 37° C.).

The pressure inside the balloon, as depicted in FIG. 3C, is typically zero during the preliminary stage, or slightly negative (in cases in which a slight vacuum is drawn), relative to the environment external to the balloon. The environment external to the balloon can include, for example, atmospheric pressure at the patient and/or internal pressure adjacent to the balloon 103 and inside the patient. In absolute terms, this pressure may translate to 15-17 PSIA—for example, in an environment in which atmospheric pressure is 14.7 PSIA and internal blood pressure adds another one or two PSIA.

At the beginning of the first phase, during the initial portions of time period 304, flow of cryogenic fluid can be started, as depicted in FIG. 3A, and a corresponding flow of exhaust from the balloon 103 can also be started. As described above, the primary purpose of this first phase can be to inflate the balloon 103 against body tissue that is to be treated. Thus, as depicted in FIG. 3C, pressure inside the balloon 103 increases relative to the pressure in the preliminary phase. This pressure may be a few PSI above the pressure outside and adjacent to the balloon. Thus, when the balloon 103 is positioned inside the heart of a patient at sea level, the pressure necessary to inflate the balloon may be in the range of 14.7 to about 20 PSIA, or in differential terms relative to the ambient pressure, 0.25 PSI or less, to about 5 PSI.

The pressure needed to inflate the balloon can depend on the material used to form the balloon. For example, very compliant materials can enable a balloon to be inflated by relatively low pressures, while stiffer balloon materials may require greater inflation pressures. In some implementations, more compliant balloons are advantageous. In addition to inflating under lower pressures, more compliant balloons may more readily conform to irregularly shaped internal structures of the patient, which may result in more efficient delivery of cryotherapy.

During the first phase, the temperature inside the balloon 103 may drop slightly, as depicted in FIG. 3B, since some heat is inherently extracted from the surrounding environment when liquid cryogen changes phase to a gas. In many implementations, however, the flow of liquid cryogen is maintained at a low enough level that the amount of heat extracted is very minimal, resulting in at most a small temperature drop relative to the nominal temperature (e.g., 0.5° C., 1° C., 5° C., etc.).

In FIG. 3A, flows of cryogenic fluid to the balloon 103 and exhaust from the balloon are depicted as being continuous. In some implementations, the balloon 103 is inflated in a different manner. For example, the balloon 103 can also be inflated by introduction of a small, discrete amount of cryogenic fluid. Some of the resulting gas can be exhausted, and some of the resulting gas can be left in the balloon 103 in order to maintain the pressure inside the balloon 103. Other flow rate profiles are possible, and any suitable flow rate profile that maintains the desired pressure and temperature can be employed.

During the second phase (e.g., the treatment phase of a cryotherapy procedure), volume of cryogenic fluid delivered to the balloon 103 can be increased, as depicted in FIG. 3A, in order to treat (e.g., cool or freeze) body tissue that is adjacent to the balloon. As depicted in FIG. 3B, temperature during the second phase drops to a cryogenically therapeutic temperature. More specifically, heat from the adjacent body tissue is absorbed by the process undergone by the cryogenic fluid as it changes state to a gas, and this extraction of heat results in the body tissue being cooled or frozen.

Turning briefly to the physiology of cryotherapy, different therapeutic results can be achieved by different levels of cooling. For example, with respect to treating atrial fibrillation by remodeling tissue of the pulmonary veins (e.g., permanently altering the electrical structure or characteristics), it may be desirable to bring tissue over the full thickness of the portion of the pulmonary vein being treated to −20° C. A typical human pulmonary vein may have a thickness in the range of 1-5 mm, so a physician may deliver cryotherapy to the pulmonary vein until it is expected that the entire thickness has reached the desired temperature (e.g., −20° C.). The temperature of −20° C. is merely provided as an example. Some tissue can be remodeled, or partially remodeled, at a higher temperature, such as −10° C., but the physician may treat beyond the temperature at which remodeling begins in order to increase the efficacy of the treatment. Other kinds of tissue can be remodeled or otherwise treated at different temperatures.

At higher temperatures (e.g., −5° C., 0° C., 5° C., or some other hypothermic value), a temporary, reversible change in the body tissue may occur. For example, with respect to the aberrant electrical pathways that can give rise to atrial fibrillation, tissue through which the electrical pathways form can be chilled to a temperature that does not permanently remodel the tissue but that temporarily disrupts the electrical pathways. This chilling, which may be referred to as cryomapping, can be used to confirm that remodeling of the intended treatment site will be efficacious, without causing other adverse side effects (e.g., a conduction block in an undesirable location). Following confirmation (e.g., through the use of electrical probes and/or stimuli), the tissue can be permanently remodeled by being cooled to lower temperatures (e.g., −10° C., −20° C. or lower temperatures).

The above examples are provided in the context of treating an electrical condition such as atrial fibrillation. The reader will appreciate, however, that the systems, apparatus and methods described herein can be employed to treat other conditions. In particular, for example, maintaining pressure inside a cryotherapy balloon between an initial positioning phase and a treatment phase can provide advantages to various cryotherapy procedures, such as procedures to treat prostate cancer or other prostate conditions, or procedures to remodel vein or artery tissue.

As depicted in FIG. 3C, pressure inside the balloon 103 during the second phase 307 can be within some threshold (+/−Δ) of the pressure inside the balloon 103 within the first phase 304. That is, as described above, the pressure inside the balloon 103 can be maintained at a relatively constant value between the first and second phases, such as within 1% or less, within 5%, within 10%, within 25%, etc. By maintaining the pressure inside the balloon portion at a relatively constant value between initial positioning and treatment phases, the balloon 103 may be less likely to become dislodged from its initial location than if the pressures between the initial positioning phase and the treatment phase are not actively controlled.

In FIG. 3A, the flow rate of exhaust from the balloon 103 is depicted as substantially tracking the flow rate of cryogenic fluid to the balloon 103. The rates may be proportional in many implementations, but the reader will appreciate that the units of flow are typically different between the flow rates of cryogenic fluid to the balloon 103 and the flow rate of exhaust from the balloon 103. That is, when a cryogenic fluid is employed that changes state to a gas inside the balloon 103, the volume occupied by the gas will typically be many times larger than the volume occupied by the same amount cryogenic matter in liquid form. Thus, for a cryogenic compound having an expansion rate of 60 (e.g., where one unit of liquid expands to 60 units of gas), the exhaust flow rate may be 60 times that of the cryogenic flow rate, when a constant pressure is maintained within the balloon. Flow rates may have different proportions for other cryogenic compounds having different expansion ratios (e.g., 1:10, 1:30, 1:100, 1:600, 1:5000, etc.).

Figure 4:
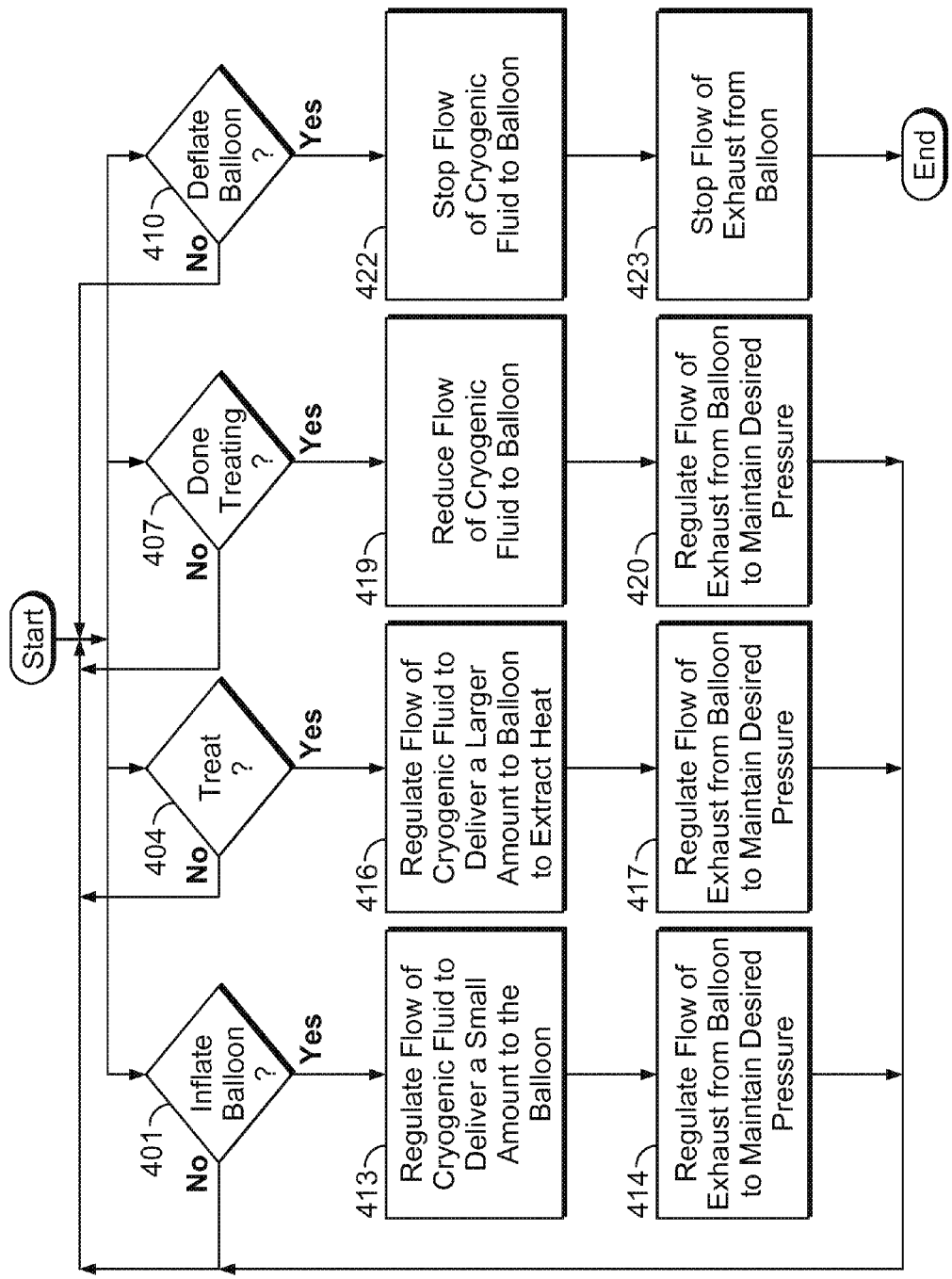
FIG. 4 is a flow diagram illustrating an example method of controlling pressure and temperature in a balloon catheter.

FIG. 4 is a flow diagram illustrating an example method 400 of controlling pressure and temperature in the balloon 103. In some implementations, the method 400 is implemented by the controller 228 shown in FIG. 2A. As shown in one implementation, and with reference to the preceding figures, the method 400 can include various decision elements that determine whether the balloon 103 is to be inflated (401) or deflated (410), whether a first treatment phase is to be performed (404) or whether a second treatment phase is to be performed (407). The decision elements can, in some implementations, be evaluated based on user input received by the controller 228. For example, during a cryotherapy procedure, a physician may provide input to the controller 228 (e.g., through a command entered through a user interface of a computer device, through manual actuation of a switch, etc.) to inflate the balloon 103 or initiate a particular phase of treatment.

When it is determined (401) that the balloon is to be inflated, the controller 228 can regulate (413) flow of cryogenic fluid to the balloon to deliver a small quantity of the cryogenic fluid, or to continuously deliver cryogenic fluid at a low flow rate. The rate can be sufficient to inflate the balloon but can be kept low enough to minimize any cooling effect within the balloon. In some implementations, with reference to FIGS. 2A and 2B, the controller 228 can regulate (413) the flow of cryogenic fluid by controlling a valve 229 between a cryogenic fluid source 230 and a cryogenic supply lumen 212. The valve 229 in such an implementation can be controlled in an open-loop or closed-loop manner. In closed-loop control scenarios, the controller 228 can employ pressure sensors, such as sensors P1 and P2 to control the flow (e.g., based on a correlation between pressure and mass delivered). Alternatively, the controller 228 can employ other kinds of metering or sensing devices, such as a mass-flow meter to regulate (413) an amount of cryogenic fluid supplied to the balloon 103.

A corresponding flow rate of exhaust from the balloon 103 (e.g., exhaust gas produced when cryogenic fluid is released into and changes state in the balloon 103) can be regulated (414). The exhaust flow rate can be regulated (414) in a manner that develops a desired pressure inside the balloon 103 (e.g., a pressure necessary to inflate the balloon 103). For example, in some implementations, it may be desirable to inflate the balloon with a pressure of 0.25 to about 5.0 PSI above an ambient pressure at a treatment site inside a patient (e.g., a pressure corresponding to atmospheric pressure and internal blood pressure of the patient at the treatment site). In absolute terms, that pressure may be in the range, for example, of about 15 PSIA to about 20 PSIA. To develop and maintain such a pressure, the controller 228 can employ one or more pressure sensors, such as sensors P3 and P4, or other appropriate metering or sensor devices.

When it is determined (404) that cryotherapy treatment is to be performed, the controller 228 can regulate (416) flow of cryogenic fluid to the balloon 103 to deliver a larger flow of the cryogenic fluid—in particular, a sufficient flow rate to remove a therapeutic quantity of heat from body tissue being treated. For example, the mass of cryogenic fluid delivered to the balloon 103 may be sufficient to remove enough heat to freeze a circumferential band of body tissue that is in contact with the balloon (e.g., tissue corresponding to the ostium or antrum of a patient's pulmonary vein, in a cryotherapy treatment for atrial fibrillation) to −20° C., and to a depth of 5 mm. The mass of cryogenic fluid delivered to the balloon 103 may be further controlled such that the heat is removed within a desired period of time (e.g., for an average human patient, adult male patient, adult female patient, adolescent patient, infant patient, etc.), such as within five minutes, four minutes, three minutes, etc. The amount of heat that is to be removed, and thus the amount of cryogenic fluid that is supplied to the balloon, may vary by procedure. For example, more or less tissue may need to be frozen in a cryotherapy procedure to treat prostate cancer than in a cryotherapy procedure for treating atrial fibrillation.

As described above, the controller 228 can regulate (416) the flow of cryogenic fluid by controlling the valve 229 between a cryogenic fluid source 230 and a cryogenic supply lumen 212 in a closed- or open-loop manner and in conjunction with various pressure sensors, or employing other appropriate metering or sensing devices.

A corresponding flow rate of exhaust from the balloon 103 (e.g., exhaust gas produced when cryogenic fluid is released into and changes state in the balloon 103) can be regulated (417) such that the pressure inside the balloon 103 is maintained within a threshold value of the pressure during the first phase. As described above, the controller 228 can control the exhaust rate with the valve 231, and in conjunction with pressure sensors P3 and P4. Alternatively, the exhaust flow rate could be controlled in other ways. For example the controller 228 may directly control a vacuum source 227, and the controller 228 may employ other types of sensors in place of the pressure sensors P3 and P4, such as, for example, a mass flow meter (not shown in the figures).

When it is determined (407) that the treatment phase is complete, the controller 228 can reduce (419) the flow of cryogenic fluid to the balloon 103—for example back to a rate comparable to that in the inflation phase. The controller 228 can simultaneously reduce (420) the flow rate of exhaust out of the balloon to maintain pressure inside the balloon to within a threshold value of the level in the other phases. By maintaining the pressure a substantially consistent value as before, the balloon may remain positioned and inflated at the treatment site.

In some implementations, an additional treatment cycle can then be initiated. For example, it can sometimes be advantageous to freeze body tissue that is to be treated, allow the tissue to warm back up (e.g., close to its nominal temperature, or to some temperature that is higher than a cryomapping temperature), then treat the tissue again. In such scenarios, two or more treatment cycles may increase the efficacy of the overall cryotherapy procedure.

When it is determined (410) that the balloon is to be deflated, any continuous flow of cryogenic fluid to the balloon 103 can be stopped (422), and the exhaust flow can also be stopped (423) at an appropriate time. In some implementations, the cryogenic fluid flow is stopped before the flow of exhaust, in order to draw a vacuum in the balloon that is sufficient to fully deflate the balloon. After the balloon is deflated, it can be withdrawn from the patient's body. Alternatively, the balloon could be moved to a different treatment site, re-inflated, and the treatment process can be repeated. In other implementations, the balloon 103 can be moved to one or more other treatment sites without being fully deflated. In some cryotherapy procedures, such as those involving atrial fibrillation, it may be advantageous to treat multiple sites (e.g., each of four pulmonary veins that are present in a typical human patient), on or more times, within a single procedure.

A number of implementations have been described. Nevertheless, it will be understood that various modifications may be made without departing from the spirit and scope of this document. Accordingly, other implementations are within the scope of the following claims.

What is claimed is:

1. A method of performing a cryotherapy procedure, the method comprising:
   introducing a cryotherapy balloon catheter at a treatment site inside a patient's body;
   during a first phase of a cryotherapy procedure, using a pressure source to inflate a first distal balloon portion of the cryotherapy balloon catheter, independently of a release of cryogenic fluid into the first distal balloon portion, to expand the first distal balloon portion and to cause an initial pressure to be maintained inside the first distal balloon portion that is sufficiently high to cause an outer wall of the first distal balloon portion to be pressed against body tissue at the treatment site;
   starting a flow of cryogenic fluid to the first distal balloon portion and a corresponding flow of exhaust from the first distal balloon portion; and
   regulating, during a second phase of the cryotherapy procedure, flow of cryogenic fluid to and exhaust from the first distal balloon portion to cause a) a temperature inside the first distal balloon portion to reach a value sufficient to deliver therapeutic levels of cryotherapy to the body tissue, and b) a second-phase pressure to be maintained that is within a threshold value of the initial pressure.

2. The method of claim 1, wherein the threshold value is substantially 10% of the initial pressure.

3. The method of claim 1, wherein the threshold value is substantially 5% of the initial pressure.

4. The method of claim 1, wherein the initial pressure is in the range of 10-20 pounds per square inch absolute (PSIA).

5. The method of claim 1, wherein the threshold value is substantially 0.5 pounds per square inch absolute (PSIA).

6. The method of claim 1, wherein using the pressure source to inflate the first distal balloon portion during the first phase comprises regulating flow of inflation fluid to the first distal balloon portion of the cryotherapy balloon catheter such that a temperature on the outer wall is maintained that does not substantially cool the body tissue beyond its nominal temperature.

7. The method of claim 1, wherein regulating during the second phase comprises regulating flow of cryogenic fluid to and exhaust from the first distal balloon portion of the cryotherapy balloon catheter such that the temperature on the outer wall is sustained at −80° C.+/−10° C.

8. The method of claim 1, wherein regulating during the second phase comprises regulating flow of cryogenic fluid to and exhaust from the first distal balloon portion of the cryotherapy balloon catheter such that a quantity of heat can be removed that is sufficient to circumferentially ablate pulmonary vein tissue of an average human adult to a depth of 5 mm within five minutes.

9. The method of claim 1, further comprising regulating, after the second phase, flow of cryogenic fluid to and exhaust from the first distal balloon portion such that minimal heat is extracted from the body tissue, to allow the body tissue to warm up.

10. The method of claim 9, further comprising at least partially deflating the first distal balloon portion, introducing the cryotherapy balloon catheter to a second treatment site, and regulating the pressure source and the flow of cryogenic fluid to and exhaust from the first distal balloon portion to repeat the first and second phases of the cryotherapy procedure at the second treatment site.

11. The method of claim 1, wherein regulating flow of cryogenic fluid to and exhaust from the first distal balloon portion comprises regulating flow of liquid nitrous oxide to the first distal balloon portion and flow of gaseous nitrous oxide from the first distal balloon portion.

12. A cryotherapy catheter comprising:
   an elongate member and an inflatable balloon at a distal end of the elongate member, the elongate member having lumens formed therein to supply inflation fluid and cryogenic fluid to a first chamber of the balloon and to channel exhaust from the first balloon chamber; and
   a controller programmed to control a first rate at which the inflation fluid is supplied to the first balloon chamber, a second rate at which cryogenic fluid is supplied to the first balloon chamber, and a third rate at which exhaust is channeled from the first balloon chamber, wherein the controller is programmed to a) inflate the balloon using a pressure source to deliver inflation fluid to develop, during a first phase of a cryotherapy procedure, a first pressure inside the first balloon chamber, and b) deliver cryogenic fluid to the first balloon chamber and exhaust from the first balloon chamber to maintain, during a second phase of the cryotherapy procedure, a pressure inside the first balloon chamber that is within a threshold value of the first pressure, at a temperature that is sufficiently low to extract heat, at a therapeutic rate, from an environment adjacent to the outer wall.

13. The cryotherapy catheter of claim 12, wherein a diameter of the elongate member is sized such that the inflatable balloon can be routed, in a deflated state, to the left atrium of an adult human patient.

14. The cryotherapy catheter of claim 13, further comprising a guidewire and corresponding guidewire lumen.

15. The cryotherapy catheter of claim 12, wherein the inflatable balloon comprises a compliant material configured to enable the balloon to inflate under a pressure of 0.5 pounds per square inch (PSI) or less above an ambient pressure that is adjacent to and outside the inflatable balloon.

16. The cryotherapy catheter of claim 12, wherein the inflatable balloon comprises an outer balloon and inner balloon that is separate from the outer balloon, wherein the inner balloon defines the first balloon chamber.

17. The cryotherapy catheter of claim 12, wherein the inflatable balloon is configured to deliver, when inflated, cryotherapy to an ostium or antrum of a human patient's pulmonary vein.

18. The cryotherapy catheter of claim 12, wherein the inflatable balloon is configured to deliver cryotherapy to a human patient's prostate.

19. The cryotherapy catheter of claim 12, wherein the controller is programmed to inflate the first balloon chamber independently of delivering cryogenic fluid to the first balloon chamber.

* * * * *